United States Patent
Schieffer et al.

(10) Patent No.: US 9,375,629 B2
(45) Date of Patent: Jun. 28, 2016

(54) METHOD AND APPARATUS FOR VISUAL SIMULATION OF EXERCISE

(75) Inventors: Shane Schieffer, Superior, CO (US);
Lucas Schieffer, Golden, CO (US);
Andrew Hamilton, Denver, CO (US)

(73) Assignee: Gusto Technologies, Inc., Golden, CO (US)

( * ) Notice: Subject to any disclaimer, the term of this patent is extended or adjusted under 35 U.S.C. 154(b) by 526 days.

(21) Appl. No.: 13/540,501

(22) Filed: Jul. 2, 2012

(65) Prior Publication Data

US 2013/0210579 A1 Aug. 15, 2013

Related U.S. Application Data

(60) Provisional application No. 61/598,100, filed on Feb. 13, 2012.

(51) Int. Cl.
| | |
|---|---|
| *A63B 71/06* | (2006.01) |
| *A63B 22/00* | (2006.01) |
| *A63B 22/06* | (2006.01) |
| *G06F 19/00* | (2011.01) |

(52) U.S. Cl.
CPC ........ *A63B 71/0622* (2013.01); *G06F 19/3481* (2013.01); *A63B 22/0076* (2013.01); *A63B 22/0605* (2013.01); *A63B 22/0664* (2013.01); *A63B 2071/0638* (2013.01); *A63B 2071/0644* (2013.01); *A63B 2210/50* (2013.01); *A63B 2220/17* (2013.01); *A63B 2225/20* (2013.01); *A63B 2225/50* (2013.01); *A63B 2230/062* (2013.01)

(58) Field of Classification Search
CPC ........... A63B 71/0622; A63B 22/0766; A63B 22/0605; A63B 22/0664; A63B 2071/0638; A63B 2071/0644; A63B 2210/50; A63B 2220/17; A63B 2225/20; A63B 2225/50; A63B 2230/062; G06F 19/3481
USPC .......................................... 482/1, 3, 8, 9, 902
See application file for complete search history.

(56) References Cited

U.S. PATENT DOCUMENTS

| | | | | | |
|---|---|---|---|---|---|
| 4,278,095 | A | * | 7/1981 | Lapeyre | 600/502 |
| 5,240,417 | A | * | 8/1993 | Smithson et al. | 434/61 |
| 5,277,678 | A | * | 1/1994 | Friedebach et al. | 482/70 |
| 5,466,200 | A | * | 11/1995 | Ulrich et al. | 482/4 |
| 5,489,249 | A | * | 2/1996 | Brewer et al. | 482/5 |
| 5,524,637 | A | * | 6/1996 | Erickson | 600/592 |
| 5,577,981 | A | * | 11/1996 | Jarvik | 482/4 |
| 5,591,104 | A | * | 1/1997 | Andrus et al. | 482/7 |
| 6,004,243 | A | * | 12/1999 | Ewert | 482/8 |

(Continued)

OTHER PUBLICATIONS

Davey, R. C., et al., "Speed, Gradient and Workrate in Uphill Running", *Journal of the Operational Research Society* (1995) 46, 43-49.

(Continued)

*Primary Examiner* — Loan H Thanh
*Assistant Examiner* — Sundhara Ganesan
(74) *Attorney, Agent, or Firm* — Blakely, Sokoloff, Taylor & Zafman

(57) ABSTRACT

A method and apparatus to receive a measure of heart rate for a user while the user is exercising on a stationary exercise device, calculate a speed of the user based on the measure of heart rate, and display on a display device viewable by the user a location of where the user would be along a selected route based on the user's speed.

15 Claims, 6 Drawing Sheets

(56) References Cited

U.S. PATENT DOCUMENTS

| | | | |
|---|---|---|---|
| 6,142,913 A * | 11/2000 | Ewert | 482/8 |
| 6,152,856 A * | 11/2000 | Studor et al. | 482/8 |
| 6,179,746 B1 * | 1/2001 | Delman | 482/6 |
| 6,244,987 B1 * | 6/2001 | Ohsuga et al. | 482/4 |
| 6,336,891 B1 * | 1/2002 | Fedrigon et al. | 482/8 |
| 6,428,449 B1 * | 8/2002 | Apseloff | 482/3 |
| 7,972,245 B2 * | 7/2011 | Temple et al. | 482/8 |
| 2005/0075213 A1 * | 4/2005 | Arick | 482/1 |
| 2006/0203090 A1 * | 9/2006 | Wang et al. | 348/143 |
| 2007/0042868 A1 * | 2/2007 | Fisher et al. | 482/8 |
| 2011/0288381 A1 * | 11/2011 | Bartholomew et al. | 600/301 |

OTHER PUBLICATIONS

Wikipedia, "Bicycle Performance", http://en.wikipedia.org/w/index.php?/oldid=497909579 7 pages.

* cited by examiner

| Gear -> | User 1 | | | | User 2 | | | |
| --- | --- | --- | --- | --- | --- | --- | --- | --- |
| | 2 | 6 | 14 | 17 | 2 | 6 | 14 | 17 |
| Watts -> | 75 | 150 | 225 | 300 | 75 | 150 | 225 | 300 |
| 1 | 115 | 143 | 169 | 181 | 106 | 141 | 178 | 191 |
| 2 | 115 | 142 | 165 | 181 | 106 | 141 | 177 | 191 |
| 3 | 116 | 142 | 169 | 181 | 106 | 141 | 177 | 191 |
| 4 | 117 | 143 | 171 | 182 | 106 | 141 | 177 | 191 |
| 5 | 117 | 142 | 170 | 182 | 106 | 141 | 178 | 193 |
| 6 | 116 | 143 | 170 | 182 | 106 | 141 | 178 | 193 |
| 7 | 117 | 143 | 171 | 182 | 106 | 141 | 177 | 195 |
| 8 | 114 | 143 | 172 | 183 | 106 | 141 | 177 | 194 |
| 9 | 112 | 142 | 172 | 183 | 106 | 141 | 177 | 195 |
| 10 | 114 | 141 | 172 | 183 | 106 | 141 | 178 | 195 |
| 11 | 115 | 139 | 172 | 182 | 106 | 141 | 178 | 195 |
| 12 | 116 | 140 | 171 | 183 | 109 | 141 | 178 | 195 |
| 13 | 117 | 142 | 170 | 183 | 111 | 141 | 177 | 196 |
| | 116 | 142 | 171 | 182 | 106 | 141 | 177 | 193 |

FIG. 5

METHOD AND APPARATUS FOR VISUAL SIMULATION OF EXERCISE

This applications claims priority to U.S. provisional patent application No. 61/598,100, filed 13 Feb. 2012, titled "SYSTEMS AND METHODS FOR HEART RATE DRIVEN SIMULATION".

TECHNICAL FIELD

Embodiments of the invention relate to exercise equipment. In particular, embodiments of the invention relate to exercising on a stationary equipment device while viewing an interactive display device that tracks a user's or exerciser's progress along a selected pre-recorded route.

BACKGROUND ART

Indoor exercise lacks the inspiration, exploration, and motivation of outdoor activity, thereby exposing users (exercisers) to boredom and increasing the probability that they will discontinue a workout program or fall short of their fitness goals.

Prior art indoor exercise equipment may provide a very limited interaction, typically based on computer-generated simulations, and fall victim to one or more of the following five shortfalls. First, most of the interactive systems utilize computer-generated simulations and not true video footage of actual, real courses. Second, the equipment defines or demands what type of exercise is to be performed. For example, a stationary bike or a bike set up on a trainer does not enable a user to hike or run, and a treadmill does not enable the user to bike and so separate pieces of exercise equipment and sensing hardware are required. Third, most exercise equipment is relatively large and heavy and thus only can be used in one location. Fourth, the workout history/data for any particular piece of exercise equipment pertains to that piece of equipment and does not transfer or follow a user to other types of physical activities and other types of exercise equipment. Lastly, these exercise systems tend to be quite costly.

What is needed is a method and apparatus providing users with an interactive experience of real roads and trails that continuously responds to them during their workout as if they were actually there, so that many of the benefits of outdoor training can be captured.

BRIEF DESCRIPTION OF THE DRAWINGS

Embodiments of the invention will be understood more fully from the detailed description given below and from the accompanying drawings of various embodiments of the invention, which, however, should not be taken to limit the invention to the specific embodiments, but are for explanation and understanding only.

FIG. 5 is a table of data that provides a translation from a user's heart rate into power, according to one embodiment of the invention.

DESCRIPTION OF THE EMBODIMENTS

Figure 1:
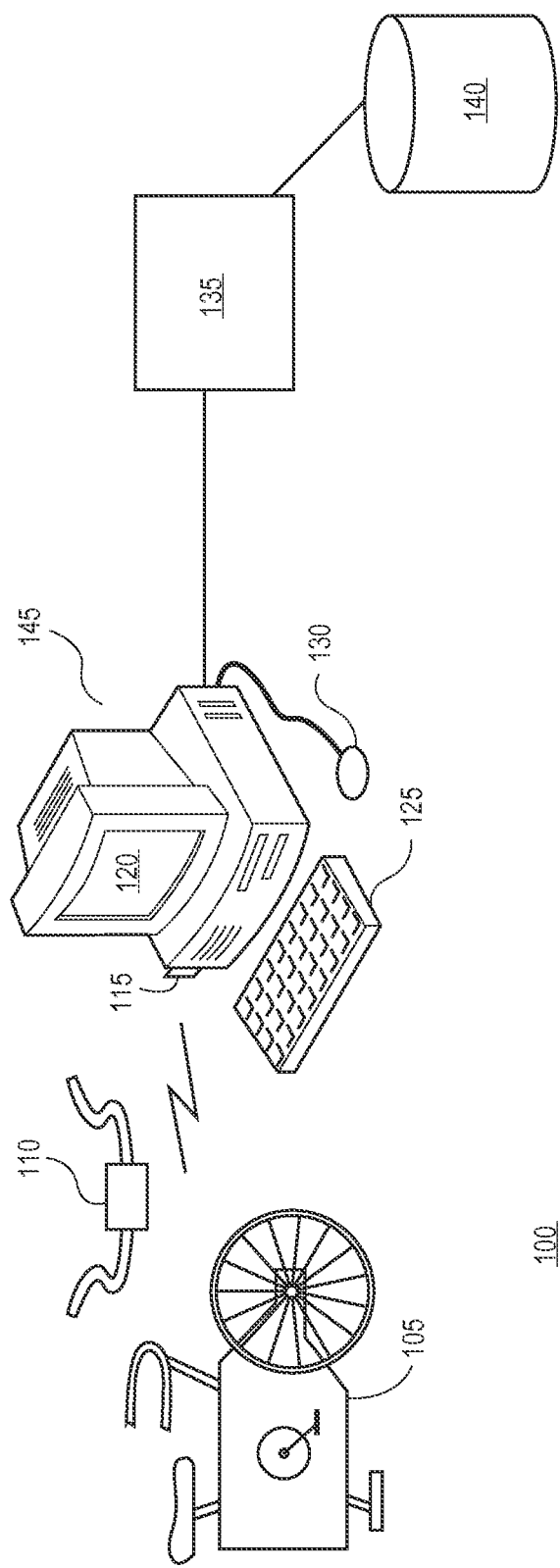
FIG. 1 illustrates an embodiment of the invention.

Embodiments of the invention enable any person (a "user" or "exerciser" herein), of any level of fitness condition, performing any sport, on any piece of fitness or exercise equipment, in any location, to simulate any pre-recorded or otherwise documented outdoor route or course they choose while accounting for the actual level of effort required to navigate the outdoor route as if they were there in person. Embodiments of the invention are used in conjunction with activities that affect heart rate, principally walking, hiking, running, biking, and rowing. In one embodiment, a user selects a course that they wish to use. For example, the user selects a pre-recorded video of an outdoor route, such as a particular stage of a grand tour bike race, e.g., a stage of the Tour de France. The course need not match the exercise machine the user is using. For example, one could choose a pre-recorded video of the Slickrock mountain bike route in Moab, Utah, even though s/he is actually running on a stationary treadmill. In all cases the user earns his or her way through the course in the sense that one's speed through the course is determined by one's level of physical condition and effort.

In one embodiment, statistics of the workout are maintained, including periodic calibrations. These statistics can be used to track frequency, duration, and intensity of workouts, and improvements in the user's conditioning over time. The user may receive notifications offering motivation or reminders of their goals as they progress, in one embodiment.

Embodiments of the invention provide a portable solution that a user can adopt directly, regardless of where the user works out or what exercise machine he or she uses. One embodiment has two principle aspects. First, the embodiment puts the user's visual experience in the forefront of what a user is achieving. Whereas many other exercise systems focus on controlling an exercise machine's resistance, incline, or speed, embodiments of the invention allow the user to control the exercise machine and select a level of difficulty suitable for his or her fitness and goals. An embodiment of the invention, in turn, plays a pre-recorded video at the speed the user would be going if the user were actually on the course given that chosen level of effort. As a user increases his or her effort, the user's speed increases in the video (assuming a consistent gradient). When the user encounters, for example, hills, a higher level of effort is required to maintain the same speed. According to the embodiment, the video is played back at the speed the user is achieving. When an embodiment indicates that a user is riding at 17.3 miles per hour, the video is played back at a frame rate that approximates 17.3 miles per hour. In this way, the user is getting an accurate simulation of a particular course without a need for an embodiment of the invention to directly control the exercise machine's settings. Second, at least one embodiment of the invention uses a counter intuitive measure to predict or calculate speed for any person, of any fitness condition, performing any sport, on any piece of fitness equipment, at any course steepness (gradient) or technical difficulty of terrain: the user's heart rate. Whereas other well known measures of user output exist, such as power and/or cadence meters for bicycling, and foot pods (that measure, for example, stride) for running, heart rate captures both cadence (or other form of speed) and resistance (or other form of difficulty) in a single measure that can be taken from a user without any physical connection to the fitness equipment itself. Traditionally heart rate is used only to record the user's effort. Heart rate is not typically thought of as a measure that predicts speed because one person's heart rate varies, and differs from others, at a given level of output depending on a number of factors, such as fitness level, and physiological differences. However, according to an embodiment of the invention, when a user's heart rate is matched with the user's fitness calibration and applied to select biology and physics equations, the user's heart rate can be used as a good predictor of the user's speed.

According to one embodiment of the invention, by combining a visual-based simulation of a route or course, such as described above, with heart rate-based algorithms to determine speed, embodiments of the invention become truly portable or mobile, and exercise device-agnostic. Embodiments of the invention may be implemented with any portable processing device such as a smart phone or tablet computer such as the Apple iPad, operating in conjunction with a software application executing on, or being presented remotely through, the processing device, to allow the embodiments to be carried with the user anywhere and used with any exercise equipment. With reference to FIG. 1, an environment 100 in which an embodiment of the invention operates, including the physical and functional components, is described.

FIG. 1 illustrates a stationary bike 105, but any form of fitness equipment, such as a treadmill, bike trainer, elliptical trainer, stair climber, rowing machine, etc., may be used according to embodiments of the invention. A user exercising on the fitness equipment wears a wireless heart rate sensor or monitor. As the user exercises, the user's heart rate is captured by the sensor and transmitted via a wireless connection according to a wireless communication protocol to a wireless heart rate receiver 115. According to one embodiment, the sensor 110 adheres to the ANT+ protocol, a protocol primarily designed for collection and transfer of sensor data, to manageable units of various types in the area of operation of sports. ANT+ (also referred to as ANT plus) is promulgated by The ANT+ Alliance, which is organized by Dynastream Innovations Inc, a subsidiary of Garmin Ltd. It is appreciated that other wireless protocols may also or alternatively be used to transmit the user's heart rate data to heart rate receiver 115. For example, sensor 110 and receiver 115 may adhere to one or more well known or standard wireless communication protocols such as Bluetooth, managed by the Bluetooth Special Interest Group, Wi-Fi (IEEE 802.11-2012), or cellular telephone mobile communication standards such as 3G or 4G promulgated by the ITU-R communications sector.

The heart rate receiver inputs the user's heart rate data into a computer processing device 145, such as a tablet computer, smart phone, or lap top computer. In one embodiment, the receiver 115 is integrated, in the portable computing device. Alternatively, the receiver can be connected, to the computer processing device via a well known interface such as a Universal Serial Bus (USB) interface. In any case, computer processing device 145 is capable of pairing with sensor 110, and can add and remove a sensor. In one embodiment, this is accomplished by providing an interface that allows putting device 145 in a listening mode to listen for ANT or ANT+ devices. Once device 145 hears a device it saves the device identification (ID), and in the future it only listens for data from that device.

It is further appreciated that receiver 115 could also be used to obtain other data from a sensor other than or in addition to a heart rate sensor located on or proximate the user or the exercise equipment, for example, the receiver 115 could receive cadence, power, stride, temperature, altitude, gradient, etc. In one embodiment, computer processing device could have or be coupled to one or more receivers in addition to receiver 115 to receive the data from a sensor, and that these receivers may use any local area communication protocol such as those described hereinabove to communicate with the sensor. In one embodiment, receiver 115 is capable to receiving sensor data from the heart rate sensor as well as multiple other sensors.

Computer processing device 145 includes or can be coupled to an electronic display device or screen 120, and may also include or be coupled to a physical or virtual (on-screen) keyboard 125. Further, a user input device 130 such as a mouse, trackpad, light pen, touch sensitive screen, or other means for visual navigation and control may be included in or coupled to the computer processing device 145. In one embodiment, the electronic display device, and/or computer processing device 145 is mounted on or in front of the exercise equipment so the user can view the display in a hands-free manner. For example, the display device may be integrated with computer processing device 145 and detachably mounted on an independent and portable stand.

In one embodiment, a user may load into a permanent or virtual storage of, or associated with, the computer processing device one or more maps or pre-recorded videos of one or more corresponding routes. For example, a user may download a map or pre-recorded video of a route from a server 135 coupled to the computer processing device via a wired and/or wireless link of an Internet connection. The server, in turn, has access to a database of maps and pre-recorded video content maintained in permanent storage device 140 accessible to the server. Additionally, according to an embodiment, terrain metadata associated with the route may also be loaded into the computer processing device's storage. The terrain metadata in one embodiment represents characteristics of the route, the speed at which it was recorded, the effort required by an operator of a camera that captured the video of the route to traverse that terrain, and the type of sport with which that effort is associated. For example, a camera operator may have been pedaling a bicycle along the route while wearing a headcam, and capturing heart rate, power, gradient, or other data indicative of the effort required by the operator to traverse the route on bike, by using ahead rate monitor or sensor and a bike computer capable of receiving and storing heart rate data from the camera operator. The data stored on the bike computer could thereafter be uploaded to permanent storage device 140 so that it is accessible by the server for download by the user along with the other characteristics of the route. In one embodiment, the data may first be statistically manipulated to "smooth" out the data to make sure it is within realistic ranges, before being uploaded.

In one embodiment, the user loads a software application into a permanent or virtual storage of, or associated with, the computer processing device. For example, a user may download the software application from a server, such as server 135 or another server, coupled to the computer processing device via an Internet connection. The server in turn accesses a permanent storage device such as permanent storage device 140 to obtain a copy of the software application for download. The software application is capable of being executed on the computer processing device to load the map or pre-recorded video of the route and associated terrain metadata and display the map or playback the pre-recorded video on the electronic display device 120 in accordance with an embodiment of the invention. In an alternative embodiment, software application interacts with a corresponding software application on the server to stream the map or video from server 135 to computer processing device 120 as the user is exercising, in real-time.

The rate of playback may be adjusted at a given instant in time according to the level of effort the user is expending exercising at that time.

The software application also allows for user input, via one or more of keyboard 125, user input device 130, and sensor 110, of user profile information, such as the user's height, weight, age, gender, fitness level, hours and type of exercise over a selected period of time, e.g., per week, resting heart rate, maximum heart rate, etc. User setup or calibration information may also be input via the same means, or collected automatically directly through the heart rate. For example, the user may perform one or more exercise tests on one or more occasions on exercise equipment 105 to establish a base line of the user's fitness level. Information from these tests, such as average heart rate for a given level of effort over a selected period of time, may be used as, or as input used to calculate, calibration information. Alternatively user calibration information may be stored in a permanent storage device such as storage device 140 and downloaded in whole or in part from a server such as server 135 that has access to storage device 140. The user's software application further includes physics or biology based algorithms, depending on the type of sport the user is participating in, that translate the user's heart rate into speed, as discussed further below.

While the embodiments illustrated in FIG. 1 and discussed above contemplate a client-server architecture environment in which the server is remotely connected to the client, for example, over the Internet, it is appreciated that the connection need not be remote. A kiosk or station, for example, in a commercial gym, may house all or substantially all of the components described in FIG. 1. In any case, the user's software application is capable of multi-user activity, wherein each user provides unique registration and profile information, logs into the application, exercises, saves his or her progress and statistics for subsequent use or viewing, and logs out.

Figure 2:
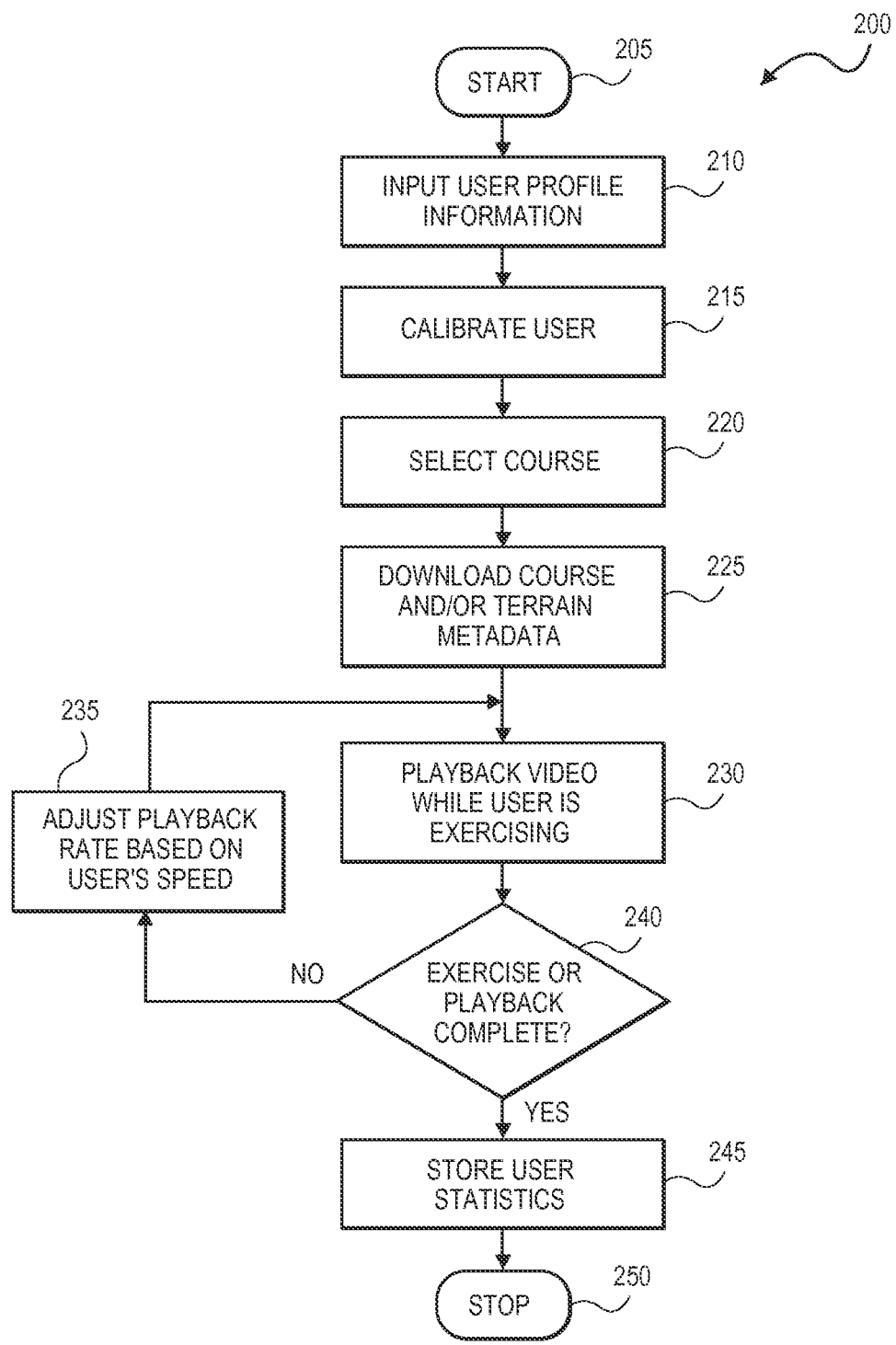
FIG. 2 provides a flow chart of a method according to an embodiment of the invention.

FIG. 2 illustrates a flow chart 200 of a method according to embodiments of the invention. The process starts at 205. A user inputs at 210 their user profile information, such as but not limited to height, weight, age, gender, and general level of physical ability. The user profile information is uploaded to a permanent storage device such as permanent storage device 140, according to one embodiment. The user wears the heart rate monitor 110, typically by strapping an adjustable band connected to the sensor around their chest so that the sensor is proximate the user's heart. The user also plugs the heart rate receiver 115 into the computer processing device 145. On the first use, the user performs a calibration at 215 that measures their heart rate at a specified level of exertion for a selected period of time. Based on this calibration, an embodiment of the invention is then able to predict the user's speed for any type of sport, and for any gradient or difficulty level, at any given heart rate. Calibration is meant to provide a way to determine the relative conditioning of a particular athlete (user). Since not every user has the same physical conditioning, adjustments may be made to determine how fast a particular user should travel at a given heart rate. According to one embodiment, the user stands still or runs a certain speed for a couple of minutes, for example, on a treadmill, and records their heart rate at that speed. An embodiment of the invention then creates a scaling factor specific to the user is used in the algorithm that translates heart rate to speed. Calibration may occur at regular intervals, say every 4 weeks or so, as the user's physical condition may change over time.

The user then selects a desired route or course at 220 for his or her workout. The route may be represented in the form a static or dynamic graphical map display or a video, either pre-recorded or otherwise generated. The course in one embodiment is downloaded from an online repository such as storage device 140 accessed by server 135, and is streamed from server 135 or stored locally on the user's computer processing device 145 for local playback. Terrain metadata associated with the selected course is also retrieved at this time. The user then chooses a sport, such as cycling if the user is exercising on a stationary bike. The sport selected by the user informs the user's software application as to which set of algorithms to use to translate heart rate into speed for the workout, which in turn controls the display of the course on the electronic display device, for example, the rate of playback of a video representation of the course. The terrain metadata also enables the user's software application to draw an elevation profile of the course.

It is appreciated that having received the user's profile information input at 210, and the calibration information obtained at 215, an embodiment of the invention now has sufficient information regarding the user's fitness level and ability or capability to maintain a certain heart rate for a certain period of time to predict the user's time to complete a course. The user in turn can benefit from this information by receiving feedback from an embodiment of the invention as to how long it would likely take the user to complete a course, for example, whether the user would qualify for the Boston Marathon based on their gender, age and fitness level. This feedback could also help the user in making the selection at 220 as to which course to download. For example, the user could gauge the degree of difficulty or time likely required to complete a particular course, and select a course accordingly based an their exercise training goals.

As the user exercises on their desired piece of fitness or exercise equipment at 230, the user's software application plays back the pre-recorded video of the selected route on the electronic display device 120, or updates a map and/or elevation profile. At 240, the software application periodically determines whether the video has ended or if the user has stopped exercising or stopped the user's software application. If the user has stopped or the video has completed, the process stops at 250. If the video has not completed or the user is still exercising, in one embodiment, the software application at 235 executes one or more algorithms utilizing the user's effort as measured by their heart rate. In another embodiment, the software application at 235 continuously executes one or more algorithms utilizing the characteristics of the terrain and the user's effort as measured by their heart rate. In one embodiment, continuous execution of the algorithms involves executing the algorithms every 1-5 seconds. It is contemplated that executing the algorithm less than every 0.10 seconds is not appropriate since heart rate does not change that quickly.

The software application, in one embodiment, also inputs data from the user's profile provided at 210 and calibration provided at 215 into the one or more algorithms. The algorithms use one or more of the data, the terrain characteristics, and heart rate to convert the user's effort into a speed at which the user is traveling while exercising on the exercise equipment. This speed is compared to the speed at which the video was originally recorded. In one embodiment, the frame rate is changed to match the speed at which the user is traveling. In another embodiment, a stop motion animation tool may be used to present those frames of video at a particular rate with greater control over when and for how long each frame of video is presented. In yet another embodiment, a multiplier is calculated that changes the frame rate of the video to match the speed at which the user is traveling. For example, the user may be calculated as traveling at a speed of 12 miles per hour and that section of the video may have been recorded at a speed of 18 miles per hour, thus the calculated multiplier is 0.66. This multiplier is then applied to the video playback function to adjust the speed of the video to match the speed of the user.

It is appreciated given the above discussion that the video playback is adjustable according to an embodiment of the invention. One embodiment contemplates the ability to play video (e.g., .mp4 video) at various speeds, from 0 speed (video stopped) to 4 times the normal speed or frame rate. Accordingly, while the video is playing, an event may be triggered every second or so, depending on processor capability. At each event, the speed at which to play the video is determined. This determination is based on the current heart rate and the current gradient (the latter being obtained from data embedded in the video), which are provided as input into an algorithm that indicates the speed to play the video. It is appreciated that speed should be realistic, so for example if a user is traveling at 20 mph, and the new calculation says the user should be traveling at 1 mph, then the speed should decrease gradually, in as realistic manner as possible. In one embodiment, the speed may be displayed in an opaque overlay along with current heart rate and distance traveled in electronic display device 120.

Figure 3:
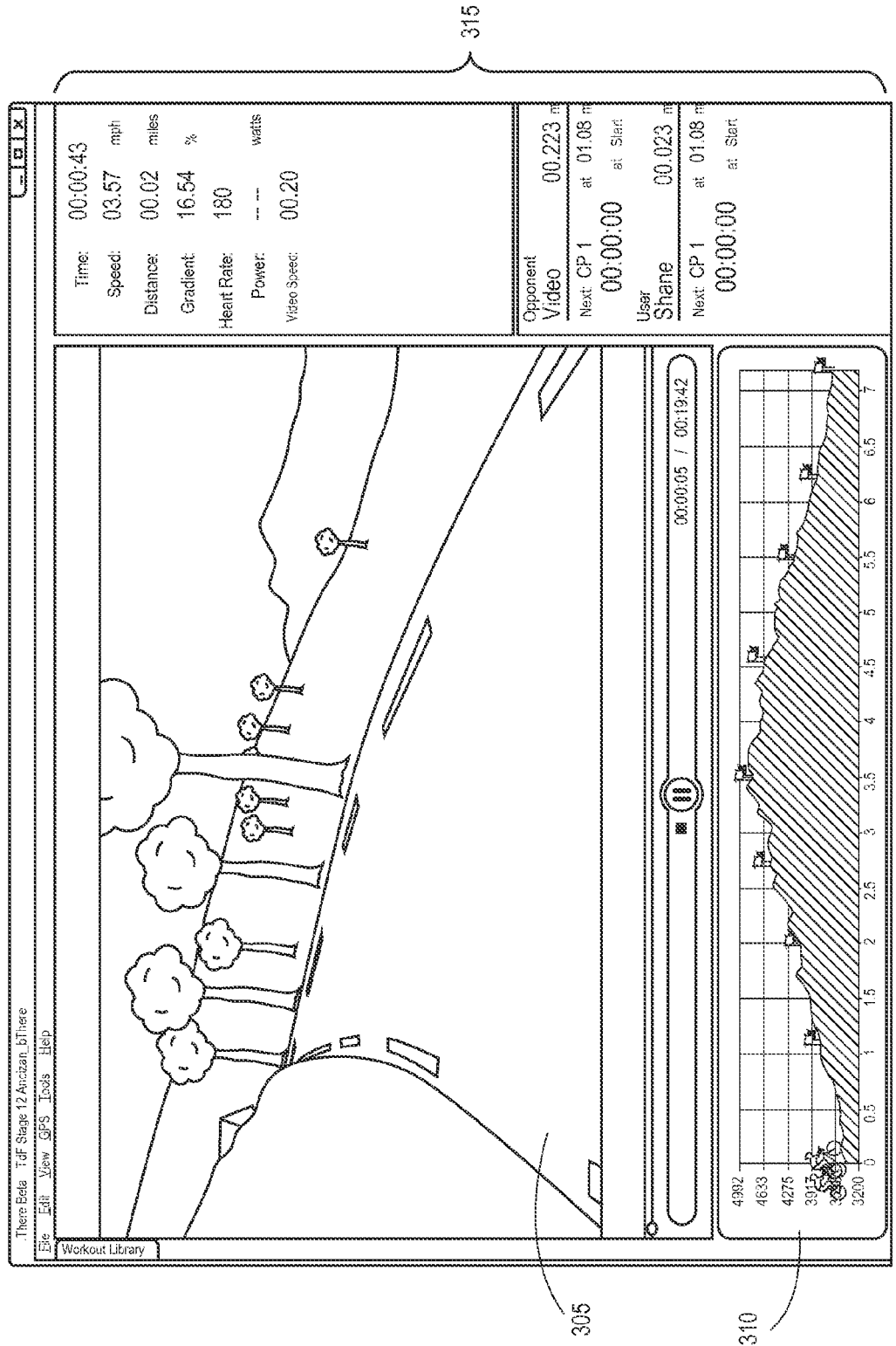
FIG. 3 provides a depiction of a visual display on an electronic display device in accordance with an embodiment of the invention.

In one embodiment of the invention, and with reference to FIG. 3, the terrain metadata and video playback 305 displayed in electronic display device 300 are synchronous in time, to provide accurate and corresponding updates of the elevation profile 310 along the course with the position of the user along the course. In one embodiment, the electronic display includes a dashboard 315 of the user's key statistics, including workout time, current speed, distance, gradient, and heart rate, for display to the user. These statistics are recorded and, at the completion of the workout or the end of the video playback of the selected route at 240, are stored for later retrieval and processing or viewing, for example, the statistics are uploaded to an online database maintained, for example, at permanent storage device 140.

As can be appreciated by the above description of embodiments of the invention, throughout the workout, the user responds to the visual stimulus provided on the display screen 120 by the user's software application. If the user desires to go faster along the displayed route, then the user must increase his cadence (speed) and/or resistance (difficulty), both of which will cause the user's heart rate to increase. Likewise, if the user reduces his effort whether by choice or inattention, and embodiment of the invention will respond by slowing or even stopping the rate of playback of the pre-recorded video of the selected route.

According to an embodiment of the invention, the user's software application will also respond differently depending on which type of route or course is selected by the user. According to embodiments of the invention, different algorithms govern the transformation of heart rate into speed for different types of exercise such as walking, hiking, running, biking, or rowing. Each algorithm is similar in that it ultimately translates heart rate into speed. However some algorithms can accomplish this directly using the user's heart rate data as the only or primary input, whereas other algorithms utilize physics and statistics to convert heart rate data into speed.

Figure 4A:
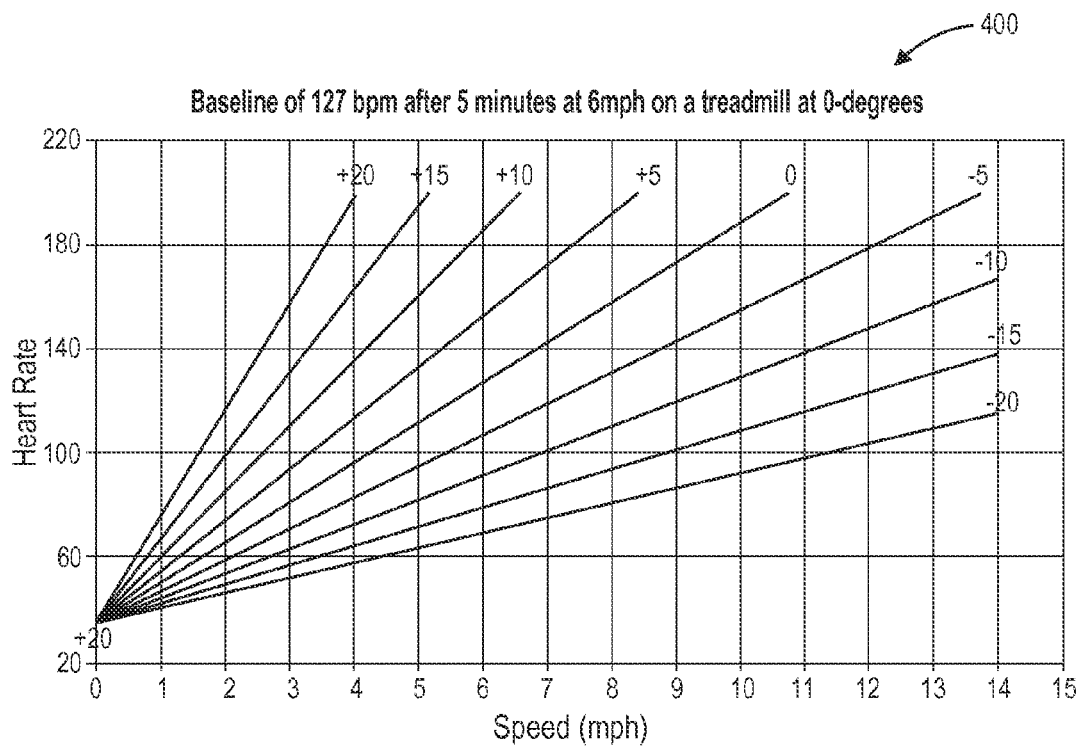
FIG. 4*a* provides a graphic depiction of a baseline physiology according to an embodiment of the invention.
Figure 4B:
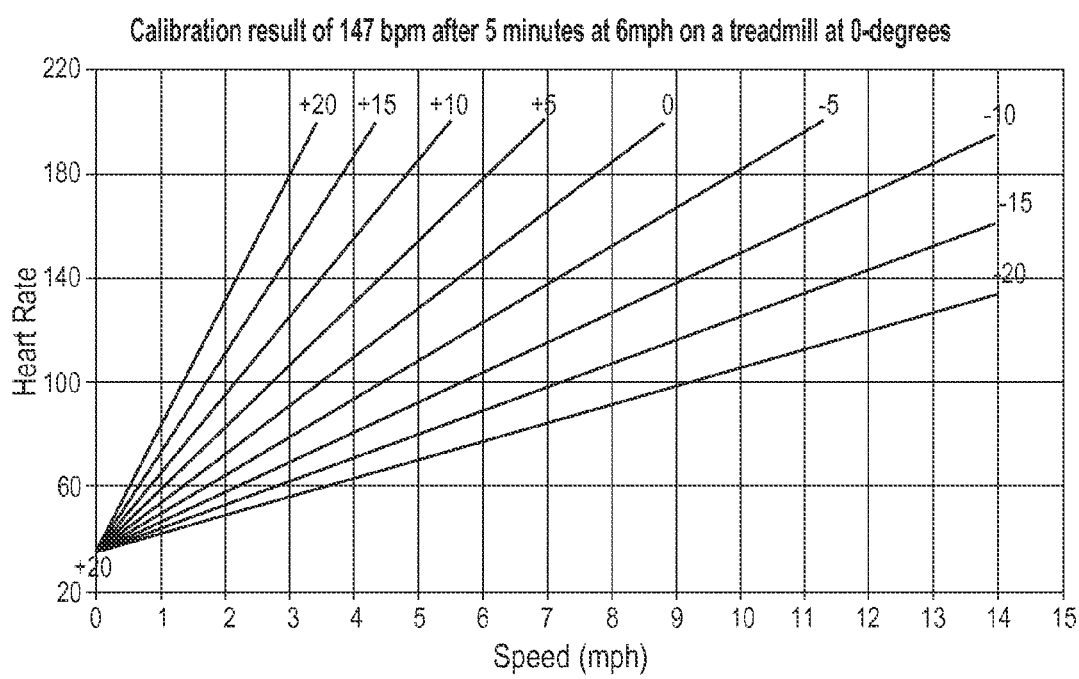
FIG. 4*b* provides a graphic depiction of a user's fitness level according to an embodiment of the invention

According to an embodiment of the invention, the user's software application manipulates the frame rate (e.g., the number of frames displayed per second) of the video as it is played back such that it matches the speed of the user based on the user's level of exertion, the user's level of fitness, and the terrain. The speed of the user is calculated based on the user's heart rate. The user's calibration provides insight into the efficiency of his body as it operates compared to that of a baseline physiology. For running, hiking, and walking, the user's heart rate is translated directly to speed. This can be obtained directly from a chart such as the comparison of the baseline physiology graphically depicted at 400 in FIG. 4A to a user's heart rate at different speeds as graphically depicted at 405 in the FIG. 4B.

Figure 6:
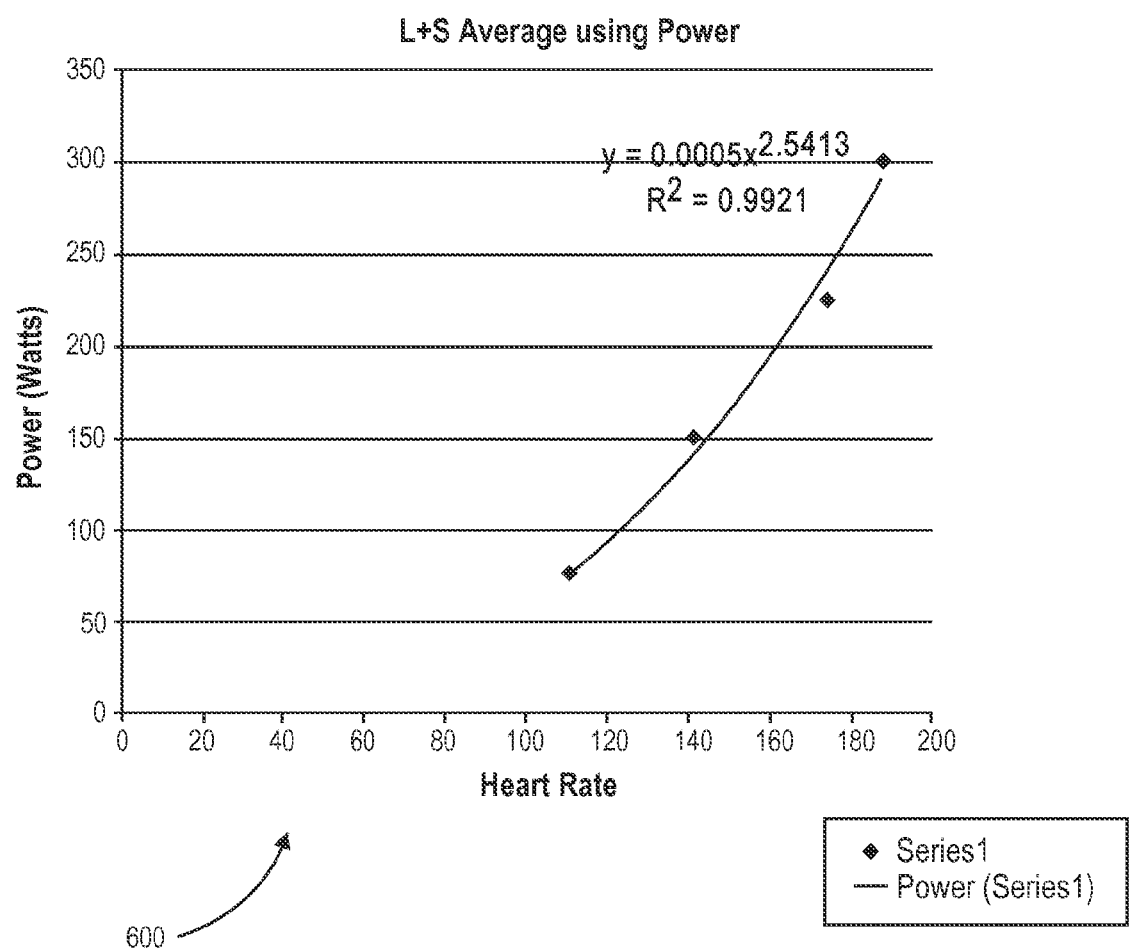
FIG. 6 provides a graphic depiction of translating a heart rate (in beats per minute) into power (in watts) according to an embodiment of the invention.

For biking, in one embodiment, the heart rate is first translated to power (for example, as measured in watts). FIG. 5 illustrates a table 500 that provides a translation from a user's heart rate into power, according to one embodiment. Thirteen heart rate samples are taken for each of two users—user 1 (510) and user 2 (520)—at different wattage settings (530) of 75, 150, 225 and 300 watts, over a period of time, for example, 5 minutes. From these samples, a particular heart rate is determined for a particular wattage setting. For example, user 1 has an average heart rate of 116 beats per minute (505) at a power setting of 75 watts, while user 2 has an average heart rate of 106 beats per minute (525) at a power setting of 75 watts. The user's software application can either perform a table look up or execute a representative function, such as graphically depicted at 600 in FIG. 6, to obtain power from the user's heart rate, considering their physical calibration in relation to the baseline.

The user's power (measured in watts) is, in turn, provided as input into a physics equation that accounts for the rider's weight, bike weight, cross-sectional surface area (for wind resistance), rolling resistance, and current gradient. This equation solves for power. In one embodiment, there is a well-known equation that gives the power required to push a bike and rider through the air and to overcome the friction of the drive train:

$$P = gmV_g(K_1+s) + K_2V_a^2V_g$$

Where P is in watts, g is earth's gravity, $V_g$ is ground speed (m/s), in is bike/rider mass in kg, s is the grade (m/m), and $V_a$ is the rider's speed through the air (m/s), $K_1$ is a lumped constant for all frictional losses (tires, bearings, chain), and is generally reported with a value of 0.0053. $K_2$ is a lumped constant for aerodynamic drag and is generally reported with a value of 0.185 kg/m.

When solved for velocity it creates a very processor intensive formula. Thus, one embodiment of the invention uses the well-known Newton's Method to solve for velocity in a more processor-efficient manlier. An example of such follows for biking.

Assume:

User current heart rate: 178 beats per minute (BPM)

User calibration: 135 BPM (as obtained, for example, from a treadmill test)

Biking algorithm heart rate (HR) baseline: 147 (see FIG. 4)

User weight: 180 pounds (LBS)

Bike weight: 20 LBS

Deriving speed from heart rate:

1. Take the Biking algorithm HR baseline (147 bpm) and divide by the user's calibrated heart rate (147/135=1.09=calibration multiplier)
2. Take user's current heart rate and multiply by the calibration multiplier (178*1.09=194=adjusted heart rate)
3. Input the adjusted heart rate into a formula that predicts power (0.005*194^2.5413=325.8 watts)

4. Convert the user and bike weight to metric ((180+20) *0.4536=90.72 kg)
5. Use newton's method to solve for velocity:

Given:

Assumed Values

| | |
|---|---|
| 9.8 | g, Defined as: Gravity (meters/second^2) |
| 0.005 | Kr, Defined as: Rolling Resistance |
| 0.2325 | Ka, Defined as: Air Resistance |
| 0.95 | te, Defined as: Transfer Efficiency From the Course Recording |
| 0.074 | s, Defined as: Gradient (m/m) |

Virtual User

| | |
|---|---|
| 90.72 | Mu, Defined as: Mass of virtual user |
| 325.8 | Pu, Defined as: User power at gym For the Equation |
| 20 | Vu, Defined as: Initial Velocity Guess (meters/second) |
| 0.1 | Tolerance |

Therefore:

Newton's Method, Iteration 1:

| | |
|---|---|
| 2,955.2 | function: Vu * (Ka * Vu^2 + (Mu * g * (Kr + s))) − te * Pu |
| 349.2 | derivative: 3 * Ka * Vu^2 + Mu * g * (Kr + s) |
| 11.5 | New velocity: Vu − function/derivative |
| 8.5 | Difference between last guess and new velocity |
| No | Is the difference within tolerance? |

Newton's Method, Iteration 2:

| | |
|---|---|
| 858.0 | function: NewVelocity * (Ka * NewVelocity^2 + (Mu * g * (Kr + s))) − te * Pu |
| 163.1 | derivative: 3 * Ka * NewVelocity^2 + Mu * g * (Kr + s) |
| 6.3 | New velocity: NewVelocity − function/derivative |
| 5.3 | Difference between last guess and new velocity |
| No | Is the difference within tolerance? |

Newton's Method, Iteration 3:

| | |
|---|---|
| 188.9 | function: NewVelocity * (Ka * NewVelocity^2 + (Mu * g * (Kr + s))) − te * Pu |
| 97.7 | derivative: 3 * Ka * NewVelocity^2 + Mu * g * (Kr + s) |
| 4.3 | New velocity: NewVelocity − function/derivative |
| 1.9 | Difference between last guess and new velocity |
| No | Is the difference within tolerance? |

Newton's Method, Iteration 4:

| | |
|---|---|
| 14.7 | function: NewVelocity * (Ka * NewVelocity^2 + (Mu * g * (Kr + s))) − te * Pu |
| 83.4 | derivative: 3 * Ka * NewVelocity^2 + Mu * g * (Kr + s) |
| 4.2 | New velocity: NewVelocity − function/derivative |
| 0.2 | Difference between last guess and new velocity |
| No | Is the difference within tolerance? |

Newton's Method, Iteration 5:

| | |
|---|---|
| 0.1 | function: NewVelocity * (Ka * NewVelocity^2 + (Mu * g * (Kr + s))) − te * Pu |
| 82.4 | derivative: 3 * Ka * NewVelocity^2 + Mu * g * (Kr + s) |
| 4.2 | New velocity: NewVelocity − function/derivative |
| 0.0 | Difference between last guess and new velocity |
| Yes | Is the difference within tolerance? |
| 4.2 | Predicted speed (meters/second) |
| 9.3 | Predicted speed in mph |

Thus, a user with a current heart rate of 178 BPM, who was calibrated at 135 against a baseline of 147, who weighs 180 lbs, riding a bike that is 20 lbs, up a 7.4 degree incline, is predicted to be traveling at 9.3 mph. Following this same method, a user with the same statistics except that s/he is on a flat (0-degree incline) section of the course would be traveling 23.3 mph.

Running:
Calculations are described in "Speed and Gradient in Uphill Running", R. C. Davey, M. Hayes, and J. M. Norman, University of Sheffield, Journal of the Operational Research Society (1995) 46, 43-49, incorporated herein by reference in it's entirety.

Power-Based Course Modeling:

Taking the example of mountain biking, it can be observed that there is a greater degree of complexity in modeling the factors that demand power by a rider. One example is that a varying surface type will continuously change power demands. Such surfaces include, but are not limited to deep loose sand, gravel, mud, water crossings, and sections of road or concrete. Further, obstacles in various forms require additional power as well. Obstacles include, but are not limited to rocks, logs, roots, washboard, or even wind. These are not easily accounted for in the above physics equation because the above equation is assuming unchanging values of rolling resistance and air resistance. Further, the above equation requires gradient which, on some courses, may change too quickly for a recording device which, in one embodiment, may take the form of a product such as a Garmin Edge. These rapidly changing gradients are especially frequent on trails where steep short inclines, steps, ledges, or other rapidly changing terrain features may be present. In fact, as these surface, obstacle, and gradient changes combine it becomes difficult to discern one factor from another, record each separately, and account for them individually in the above equation. A technique is thereby needed to capture and replicate the effort required for the rider to traverse a course across its many features. On these occasions one may prefer to record the actual power output in watts that were required at the time of recording a course. In one embodiment this may be achieved using a product such as the PowerTap. In another embodiment this may be done by measuring the power required by an electric or gas motor. This can be done for any sport which power can be measured or predicted, which may include running and hiking. Once the power profile of a course has been captured some data transformation may need to take place to neutralize rider-specific factors such as mass, and then create a variable used by an equation to enable a virtual user to recreate that same level of effort, and/or scale the speed of the virtual user's experience based on their conditioning and level of effort. In one embodiment we do this by taking the recorded data where the power, velocity, and mass has been captured, and solve for a combined rolling resistance and gradient variable that will provide a single, consolidated, term that we can apply to the algorithm governing a virtual user's experience. To achieve this we do the following:

Combine the ($k_1$+s) terms from the physics equation into a new variable we will call, "x".

Solve the power equation for x, resulting in:

$$X = \frac{Power - K_2 * V^3}{g * m * v}$$

This equation utilizes an assumed fixed aerodynamic resistance, which does not need to be the case, but is done here for simplicity.

The continuously-running algorithm by which the virtual user's speed is calculated can now include the above equation which will provide a new term for the resistance. The result of this term is then used in place of the ($k_1$+s) from the original equation. Thus, every time the equation runs it accounts for the changes in the consolidated resistive forces encountered on the actual course.

An example of one embodiment of these calculations is as follows:

| | Given: |
|---|---|
| | Assumed Values |
| 9.8 | g, Defined as: Gravity (meters/second^2) |
| 0.2325 | Ka, Defined as: Air Resistance |
| 1 | te, Defined as: Transfer Efficiency |
| | From the Course Recording |
| 300 | Pr, Defined as: Power (Watts) |
| 3 | Vr, Defined as: Velocity when recording the course |
| 99.8 | Mr, Defined as: Mass (KG) of videographer + shooting gear + bike |
| 0.0998 | x, Defined as: Derived (k1 + s) term calculated by: (Power − TransferEfficiency − AirResistance * Velocity^3)/ (Gravity * Mass * Velocity) |
| | Virtual User |
| 90.72 | Mu, Defined as: Mass of virtual user |
| 325.8 | Pu, Defined as: User power at gym |
| | For the Equation |
| 20 | Vu, Defined as: Initial Velocity Guess (meters/second) |
| 0.1 | Tolerance |
| | Therefore: |
| | Newton's Method, Iteration 1: |
| 3,308.13 | The equation: g * Mu * Vu * x + ka * Vu^3 − te * Pu |
| 367.7 | The equation's derivative: 3 * ka * Vu^2 + g * Mu * x |
| 11.0 | New velocity: vel − f/fp |
| 9.0 | Difference between last guess and new velocity |
| No | Is the difference within tolerance? |
| | Newton's Method, Iteration 2: |
| 959.86 | The equation: g * Mu * Vu * x + ka * Vu^3 − te * Pu |
| 173.1 | The equation's derivative: 3 * ka * Vu^2 + g * Mu * x |
| 5.5 | New velocity: vel − f/fp |
| 5.544 | Difference between last guess and new velocity |
| No | Is the difference within tolerance? |
| | Newton's Method, Iteration 3: |
| 196.25 | The equation: g * Mu * Vu * x + ka * Vu^3 − te * Pu |
| 109.5 | The equation's derivative: 3 * ka * Vu^2 + g * Mu * x |
| 3.7 | New velocity: vel − f/fp |
| 1.793 | Difference between last guess and new velocity |
| No | Is the difference within tolerance? |
| | Newton's Method, Iteration 4: |
| 10.90 | The equation: g * Mu * Vu * x + ka * Vu^3 − te * Pu |
| 98.1 | The equation's derivative: 3 * ka * Vu^2 + g * Mu * x |
| 3.55571 | New velocity: vel − f/fp |
| 0.111 | Difference between last guess and new velocity |
| No | Is the difference within tolerance? |
| | Newton's Method, Iteration 5: |
| 0.03 | The equation: g * Mu * Vu * x + ka * Vu^3 − te * Pu |
| 97.5 | The equation's derivative: 3 * ka * Vu^2 + g * Mu * x |
| 3.55538 | New velocity: vel − f/fp |
| 0.000 | Difference between last guess and new velocity |
| Yes | Is the difference within tolerance? |
| 3.6 | Predicted speed (meters/second) |
| 8.0 | Predicted speed in mph |

Heart Rate Based Modeling:

An alternative to the power-based recording is to log the heart rate of the rider/videographer as they video record a section of a route or trail, then predict the user's speed by comparing the videographer's adjusted heart rate with the user's adjusted heart rate. This method works well for many things including: technical hiking, canyoneering, mountaineering, walking on a beach, rowing, and almost any other sport where more scientific methods may be harder to implement.

It is appreciated that embodiments of the invention can be carried out without performing all the steps described above with reference to FIG. 2. For example, embodiments may provide for adjusting the frame rate at which the video is played back without the need for user calibration, physics formulas, or even terrain data. Removing these aspects of the above-described embodiments may reduce the accuracy of the user's calculated speed and therefore the quality of the video simulation, yet such an embodiment may still provide an acceptable level of experience to certain users. So too, an embodiment may forego using the online database to track user performance and still provide a desirable user experience.

In one embodiment, a foot pod may be used in conjunction with the heart rate sensor. Such an embodiment still provides a portable product with additional benefits. The foot pod may be used to provide cadence or stride data. Cadence or stride, when compared to the user's fitness calibration and current heart rate, provides insight into the resistance level or effort to which the user has set the exercise machine. Further, it can take several seconds for a change in effort to show up in a user's heart rate. Therefore sudden changes in cadence or stride may be used to predict a change in effort. An embodiment of the invention may leverage this prediction to immediately adjust the frame rate of video playback and then monitor and adjust the prediction as the change in the user's cadence or stride results in a change in the user's heart rate.

It is appreciated that embodiments of the invention need not be limited to playing back pre-recorded video of a selected course. In one embodiment, terrain-modeling log files of various formats taken from users while exercising outside may be used to replicate those workouts indoors. The terrain modeling may be in the form of GPS data, heart rate data, or power data captured by other devices, software applications, or programs. Further, instead of video playback, a graphical depiction of where a user is on a course may be provided, along with an accounting for the elevation profile, distance, and effort required. In one embodiment, the terrain modeling log file includes time stamps that may be used to compare a user's exercise time in the gym to the user's exercise time outdoors on a segment-by-segment basis.

In yet another embodiment, other types of sensors may be used in addition to or instead of a heart rate monitor, such as a power meter, in one embodiment, computer processing device 145 comprises the ability to connect to an ANT+ compatible power meter and get instantaneous power from the standard power page. However, depending on the size and configuration of the sensor, the embodiment may not be readily portable between different types of exercise equipment.

It is further contemplated that embodiments of the invention may be used in conjunction not with exercise equipment, but with weights, or without any fitness equipment at all. It is further contemplated that videos other than those pre-recorded for running/hiking/biking may also be made available, for example, coached workouts, calisthenics, and video-based game scenarios.

One embodiment of the invention may provide a progressive experience where users earn their way to better virtual gear and video courses. The upgraded gear can be modeled in the algorithms to cause an increase in the user's speed. More advanced courses, for example in terms of length or difficulty, could be earned, as could courses from locations around the world, in much the same manner as "Career mode" in the video gaming world. According to a further embodiment, users can connect to another user and race each other, set joint goals, and create peer accountability with one another.

CONCLUSION

In this description, numerous details have been set forth to provide a more thorough explanation of embodiments of the invention. It should be apparent, however, to one skilled in the art, that embodiments of the invention may be practiced without these specific details. In other instances, well-known structures and devices have been shown in block diagram form, rather than in detail, in order to avoid obscuring embodiments of the invention.

Some portions of this detailed description are presented in terms of algorithms and symbolic representations of operations on data within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, thong not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from this discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of invention also relate to apparatuses for performing the operations herein. Some apparatuses may be specially constructed for the required purposes, or may comprise a general purpose computer selectively activated or configured by a computer program stored in the computer. Such a computer program may be stored in a computer readable storage medium, such as, but not limited to, any type of disk including floppy disks, optical disks, CD-ROMs, DVD-ROMs, and magnetic-optical disks, read-only memories (ROMs), random access memories (RAMs), EPROMs, EEPROMs, NVRAMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized, apparatus to perform the required method. The required structure for a variety of these systems appears from the description herein. In addition, embodiments of the invention are not described with reference to any particular programming language. It will be appreciated that a variety of programming languages may be used to implement the embodiments of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices, etc.

Whereas many alterations and modifications of the embodiment of the invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims that recite only those features regarded as essential to the invention.

The invention claimed is:

1. A computer-implemented method comprising:
    receiving at a wireless heart rate sensor being worn by a user a measure of heart rate for the user while the user is exercising on a stationary exercise device;
    transmitting the received measure of heart rate for the user to a receiver in, or coupled with, a computing device;
    inputting the received measure of heart rate for the user from the receiver to the computing device;
    deriving at the computing device a power exerted by the user from the received measure of heart rate;
    deriving at the computing device a speed of the user based on the derived power;
    and
    displaying in a video playback of a pre-recorded video of a selected route on a display device integrated with, or coupled to, the computing device, and viewable by the user, a location of where the user would be along the selected route based on the user's speed.

2. The method of claim 1, wherein the displaying in the video playback of the pre-recorded video of the selected route the location of where the user would be along the selected route based on the user's speed is further based on a set of characteristics.

3. The method of claim 2, wherein the set of characteristics is selected from a group consisting of the user's weight, temperature, altitude, terrain, gradient, wind speed, wind direction, or a combination thereof.

4. The method of claim 1, wherein deriving the speed from the derived power comprises deriving the speed from the power according to Newton's method.

5. The method of claim 1, wherein the displaying in the video playback of the pre-recorded video of the selected route the location of where the user would be along the selected route based on the user's speed further comprises displaying a location of where the user would be on one of a map or an elevation profile of the selected route displayed on the display device.

6. The method of claim 1, wherein the displaying in the video playback of the pre-recorded video of the selected route the location of where the user would be along the selected route based on the user's speed comprises:
    calculating the location of where the user would be in the video playback of the pre-recorded video of the selected route based on the user's speed; and
    adjusting a speed of the video playback to display the calculated location of where the user would be in the video playback in accordance with the user's speed.

7. The method of claim 6,
    wherein calculating the location of where the user would be in the video playback of the pre-recorded video of the selected route based on the user's speed comprises comparing the user's speed with a speed of a recording device that captured the pre-recorded video; and wherein adjusting the speed of the video playback to display the calculated location of where the user would be in the video playback in accordance with the user's speed comprises adjusting a frame rate of the video playback to the extent the user's speed differs from the speed of the recording device.

8. The method of claim 7,
wherein calculating the location of where the user would be in the video playback of the pre-recorded video of the selected route based on the user's speed further comprises calculating a multiplier based on the difference between the user's speed and the speed of the recording device, and
wherein adjusting the frame rate of the video playback to the extent the user's speed differs from the speed of the recording device comprises applying the multiplier to adjust the frame rate of the video playback.

9. At least one machine readable non-transitory storage medium comprising a plurality of instructions that in response to being executed on a computing device, cause the computing device to:
receive from a wireless heart rate sensor being worn by a user a measure of heart rate for the user while the user is exercising on a stationary exercise device;
derive a power exerted by the user from the received measure of heart rate;
derive a speed of the user based on the derived power; and
display in a video playback of a pre-recorded video of a selected route on a display device integrated with, or coupled to, the computing device, and viewable by the user, a location of where the user would be along the selected route based on the user's speed.

10. The at least one machine readable non-transitory storage medium of claim 9, wherein to display in the video playback of the pre-recorded video of the selected route the location of where the user would be along a selected route based on the user's speed is further based on a set of characteristics, wherein the set of characteristics is selected from a group consisting of the user's weight, temperature, altitude, terrain, gradient, wind speed, wind direction, or a combination thereof.

11. The at least one machine readable non-transitory storage medium of claim 9, wherein to display in the video playback of the pre-recorded video of the selected route the location of where the user would be along the selected route based on the user's speed further comprises to display a location of where the user would be on one of a map or an elevation profile of the selected route displayed on the display device.

12. The at least one machine readable non-transitory storage medium of claim 11, wherein to display in the video playback of the pre-recorded video of the selected route the location of where the user would be along the selected route based on the user's speed comprises:
calculating the location of where the user would be in the video playback of the pre-recorded video of the selected route based on the user's speed; and
adjusting a speed of the video playback to display the calculated location of where the user would be in the video playback in accordance with the user's speed.

13. An apparatus comprising:
a heart rate receiver to receive a measure of heart rate for a user while the user is exercising on a stationary exercise device;
a computer processing device coupled to the heart rate receiver to derive from the received measure of heart rate a power exerted by the user;
the computer processing device to derive a speed of the user based on the derived power; and
a memory store in which to a pre-recorded video of a selected route;
the computer processing device to retrieve the pre-recorded video from the memory store and transmit the pre-recorded video to an electronic display device integrated with, or coupled to, the computer processing device to display a video playback of the pre-recorded video of the selected route and further to display in the video playback of the pre-recorded video of the selected route a location of where the user would be along the selected route based on the user's speed.

14. The apparatus of claim 13, wherein the electronic display device to display in the video playback of the pre-recorded video of the selected route the location of where the user would be along the selected route based on the user's speed is further based on a set of characteristics, wherein the set of characteristics is selected from a group consisting of the user's weight, temperature, altitude, terrain, gradient, wind speed, wind direction, or a combination thereof.

15. The apparatus of claim 13, wherein the display device to display in the video playback of the pre-recorded video of the selected route the location of where the user would be along a selected route based on the user's speed further comprises the display device to display a location of where the user would be on one of a map or an elevation profile of the selected route displayed on the display device.

* * * * *